(12) United States Patent
Reno (10) Patent No.: US 6,210,324 B1
(45) Date of Patent: Apr. 3, 2001

(54) LEVER RETRACTOR FOR SURGICAL FLAPS WITH HANDLE

(76) Inventor: Waldix Teixeira Reno, Rua Paissandu, 368, Centro, Guaratingueta, Sao Paulo (BR)

( * ) Notice: Subject to any disclaimer, the term of this patent is extended or adjusted under 35 U.S.C. 154(b) by 0 days.

(21) Appl. No.: 09/319,370
(22) PCT Filed: Dec. 2, 1997
(86) PCT No.: PCT/BR97/00070
§ 371 Date: Sep. 20, 1999
§ 102(e) Date: Sep. 20, 1999
(87) PCT Pub. No.: WO98/24375
PCT Pub. Date: Jun. 11, 1998

(30) Foreign Application Priority Data

Dec. 5, 1996 (BR) .................................................... 9604655

(51) Int. Cl.⁷ ...................................................... A61B 1/32
(52) U.S. Cl. .......................................................... 600/210
(58) Field of Search ....................................... 600/210, 211, 600/213, 217, 226, 234, 236, 235

(56) References Cited

U.S. PATENT DOCUMENTS

| | | | | |
|---|---|---|---|---|
| 3,998,217 | * | 12/1976 | Trumbull et al. | 600/217 |
| 4,622,955 | * | 11/1986 | Fakhrai | 600/217 |
| 4,694,826 | * | 9/1987 | Chester | 600/235 |
| 4,747,394 | * | 5/1988 | Watanabe | 600/217 |
| 5,769,781 | * | 6/1998 | Chappuis | 600/210 |

* cited by examiner

Primary Examiner—Gene Mancene
Assistant Examiner—Eduardo C. Robert
(74) Attorney, Agent, or Firm—Birch, Stewart, Kolasch & Birch, LLP (57) ABSTRACT

A surgical device used for separating tissue to expose a surgical area which comprises a plate member which is folded on itself to form a superior plate portion, an inferior plate portion and a folded portion disposed therebetween, said superior plate portion being spaced apart from the inferior plate portion for defining respective proximal and distal ends thereof and for accommodating a layer of tissue therebetween, said superior plate portion being larger than said inferior plate portion and each of said plate portions being divided into a plurality of fingers.

13 Claims, 10 Drawing Sheets

LEVER RETRACTOR FOR SURGICAL FLAPS WITH HANDLE

This application is the national phase under 35 U.S.C. §371 of PCT International Application No. PCT/BR97/00070 which has an International filing date of Dec. 2, 1997 which designated the United States of America.

BACKGROUND OF THE INVENTION

The present invention relates to a surgical retractor for separating in flaps in the body surface or in a massive organ for exposing body parts in considerable depth.

Surgical retractors are fundamental tools in the surgeon criative universe. The approach of working with long and narrow flaps of tissue constitutes laborious and tiresome work. One major difficulty is that the prior devices are unable to adequately expose the depth of a long and narrow flap made in body tissue. When one uses hooks, the flap collapses in depth with loss of the undermining level and difficult hemostasy. When one uses a malleable or laminar retractor the undermining is irregular without a very clear view. Besides, they are non ergonomic, demanding a manual effort to sustain them in position. The result is a change in the thickness of the flap with risk of vascular damage and slough of the flap.

BRIEF SUMMARY OF THE INVENTION

The present invention is directed to a surgical retractor for undermining and exposing a long flap in the body surface or in a massive organ. The object of the present invention is to provide an ergonomic and easily applicable retractor for undermining and exposing in depth a long flap of tissue, and for excising the tecidual excess with a clear view.

DETAILED DESCRIPTION OF THE INVENTION

The hold lever retractor is a surgical instrument constructed with a semi-rigid stainless steel plate folded on itself 1 to form two parallel plates 2 and 3, and provided with a handle 4 fixed to the external and proximal aspect side of the longer plate 2. It is particularly useful for body surface surgery or for large massive organ surgery, and is specifically designed for handling long flaps of tissue 5.

Figure 1:
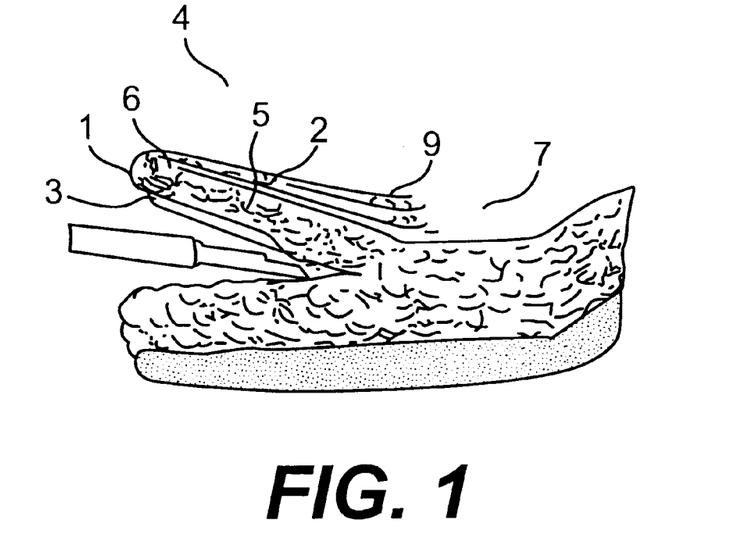
FIG. 1 is a perspective view of a hold lever retractor of the present invention used to undermine a long flap.
Figure 2:
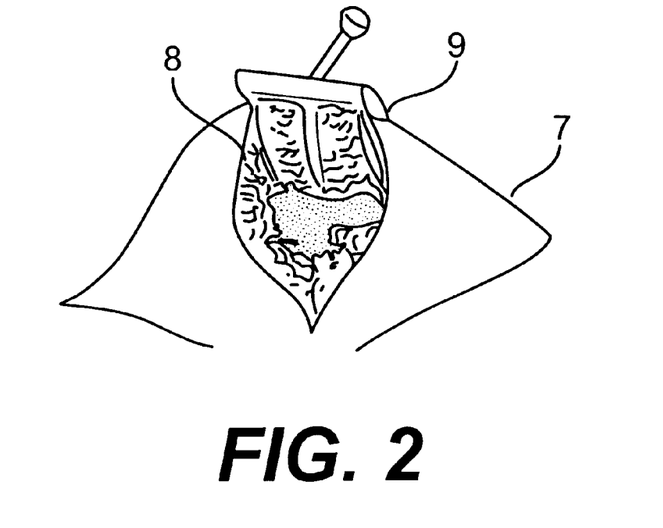
FIG. 2 is a perspective view of the hold lever retractor of the present invention used to expose the interior of a long flap.

A: after determining the flap thickness 6 and in order to make a side to side incision at this level, the inferior plate 3 is introduced into the incision so that the superior plate 2 slides over the skin 7. Once the determined extension is obtained, the handle 4 is turned forward until the retractor is supported only by its extremity 9 against the skin 7 (lever movement) as demonstrated in FIG. 1. In this way one can have a clear and ample view of the operation field 8 by lifting the flap 5 (FIG. 2).

Figure 3:
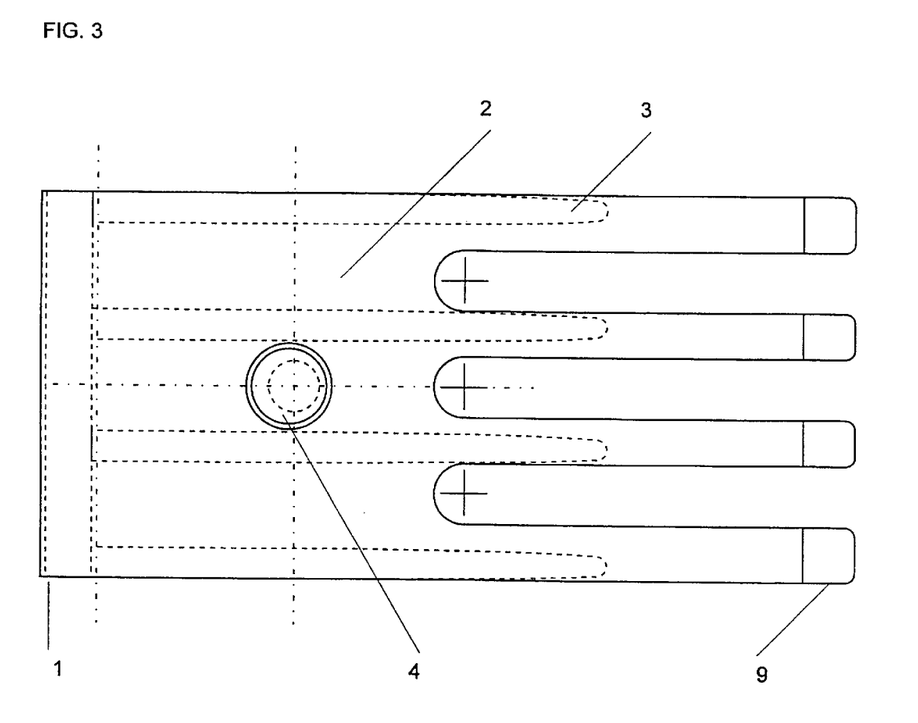
FIG. 3 is a superior view of the retractor.
Figure 4:
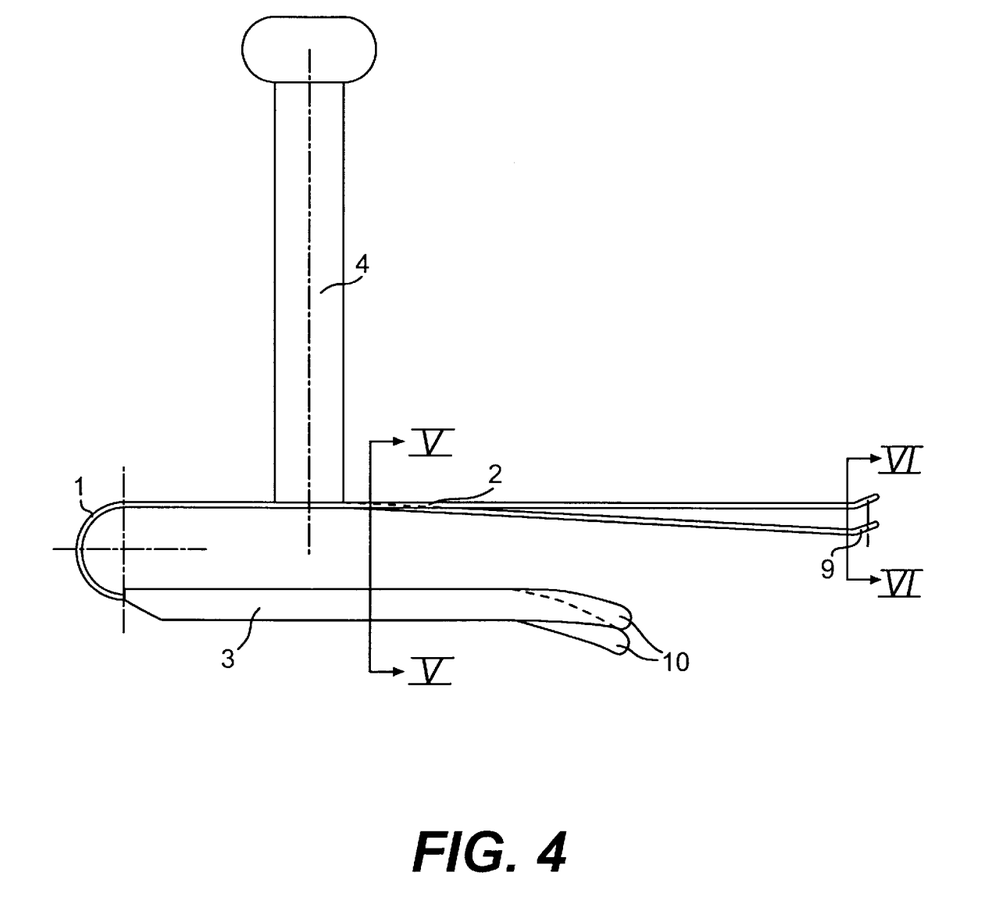
FIG. 4 is a side view of the retractor which shows the proximal cut A—A and the distal cut B—B.
Figure 5:
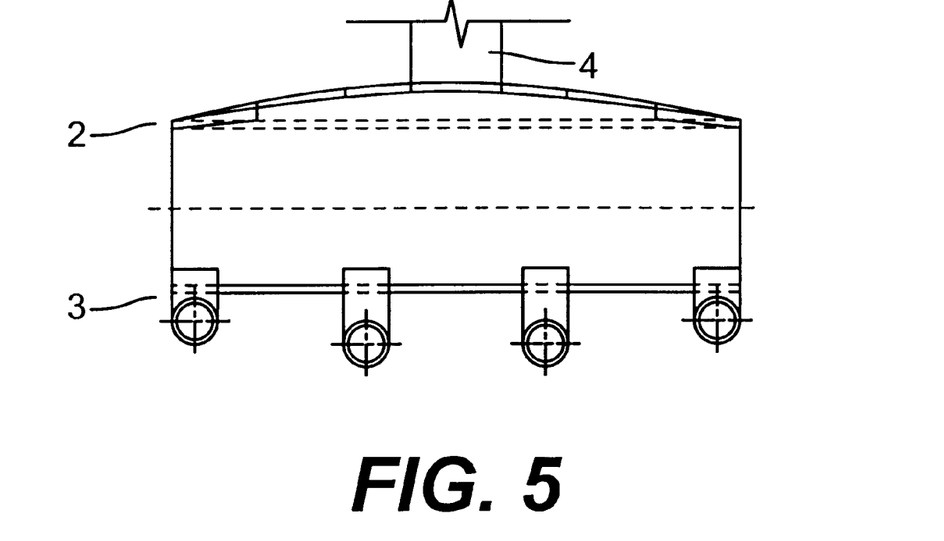
FIG. 5 is the frontal view of A—A cut.

Referring to FIG. 3, FIG. 4, and FIG. 5, this is the first retractor developed for breast surgery, but also is applicable for other types of surgeries such as face lifts and those involving large flaps of tissue. It has the superior plate 2 indentated in its distal half with the central indentations more elevated than the lateral indentations CUT B—B, and all of them flattenned and angulated up in their extremities 9. Its inferior plate 3 is shorter, narrower and totally indentated. These indentations are cylindrical, assymmetric with the lateral indentations more elevated than the medial CUT A—A, and with the extremities 10 slight tilted downward and sharp for penetrate the tissues as easily as lipoaspiration cannulas.

Figure 6:
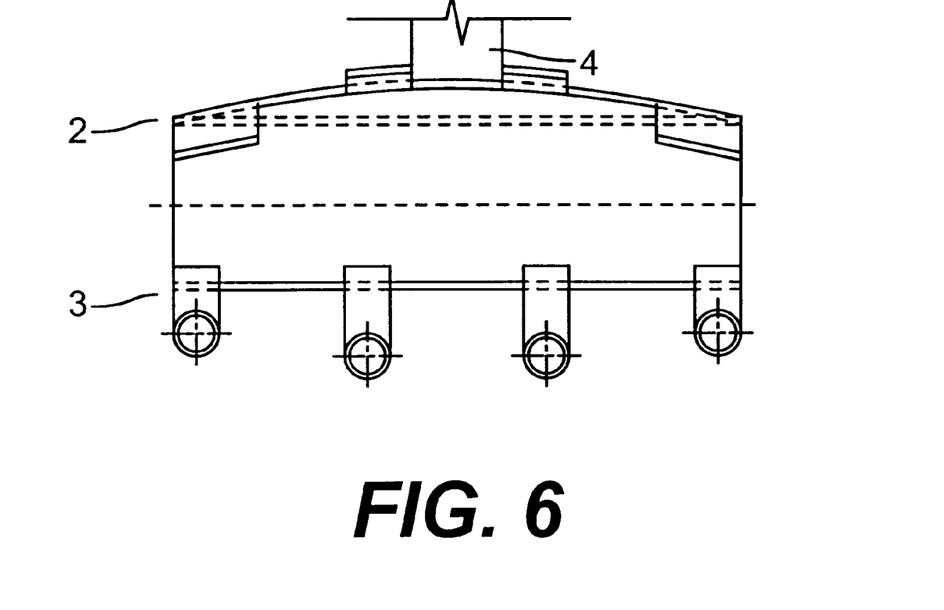
FIG. 6 is the frontal view of B—B cut.
Figure 7:
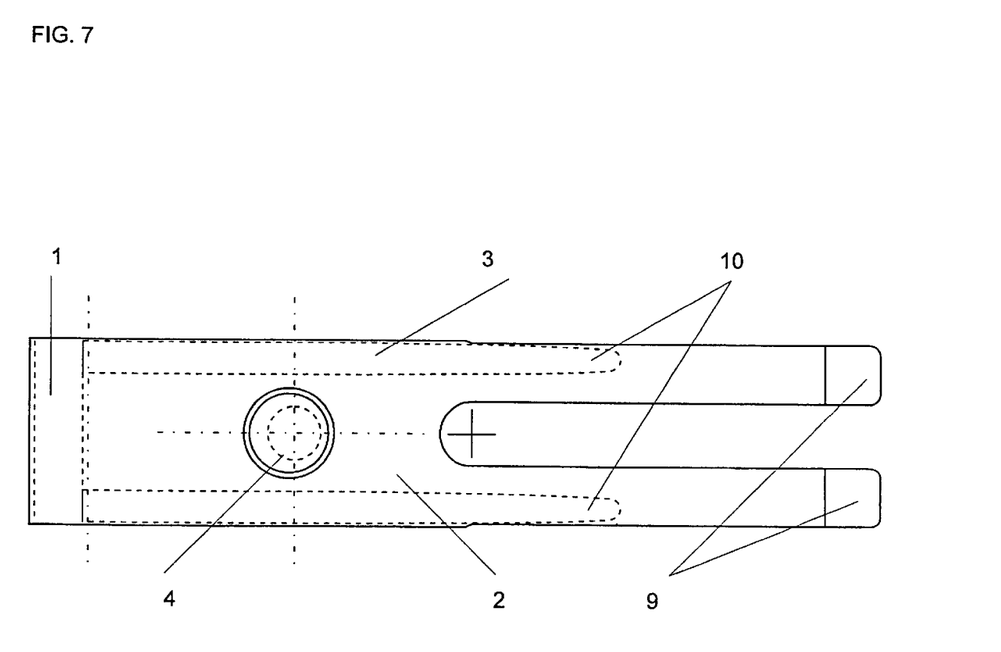
FIG. 7 is a superior view of a modified form of the retractor of the present invention.
Figure 8:
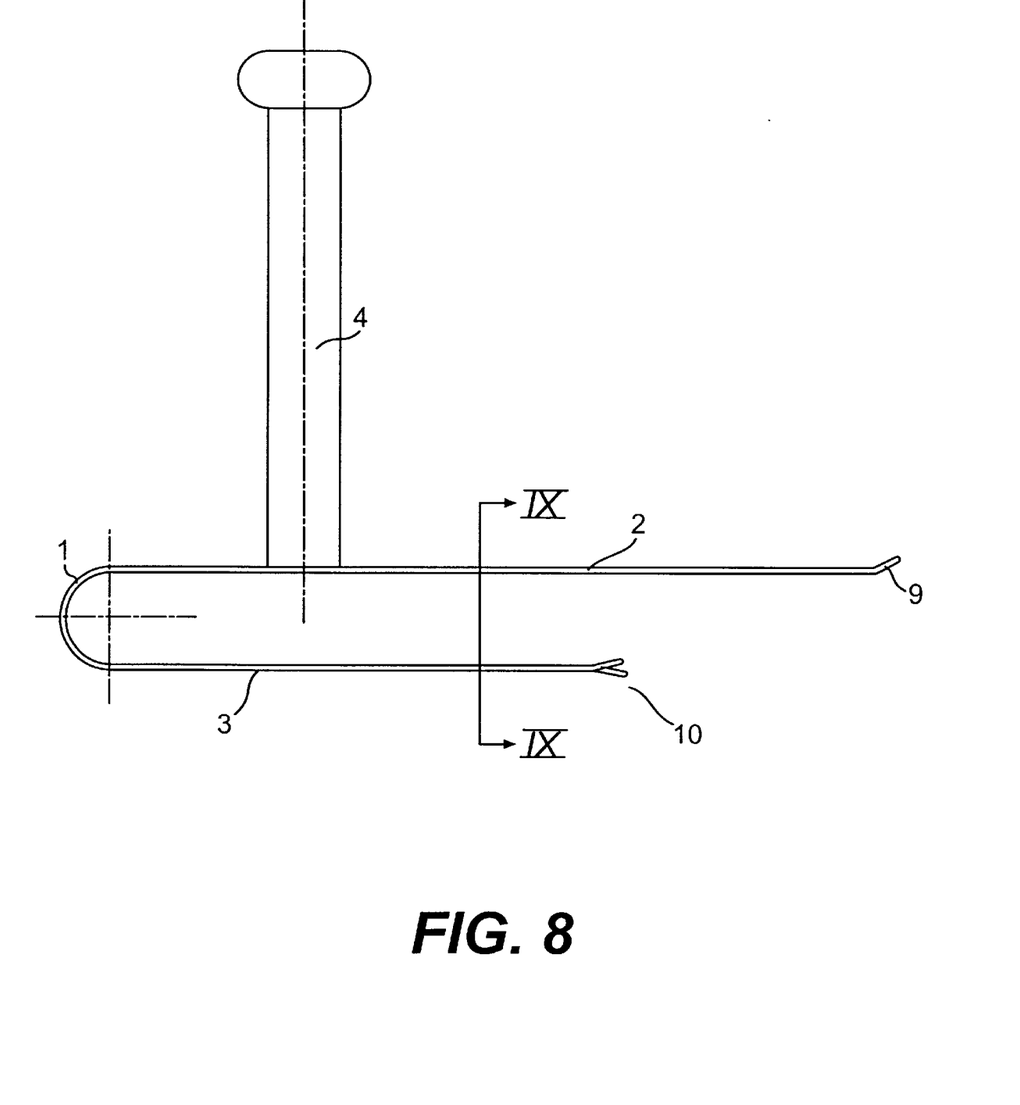
FIG. 8 is a side view of a modified form that shows the cut A—A.
Figure 9:
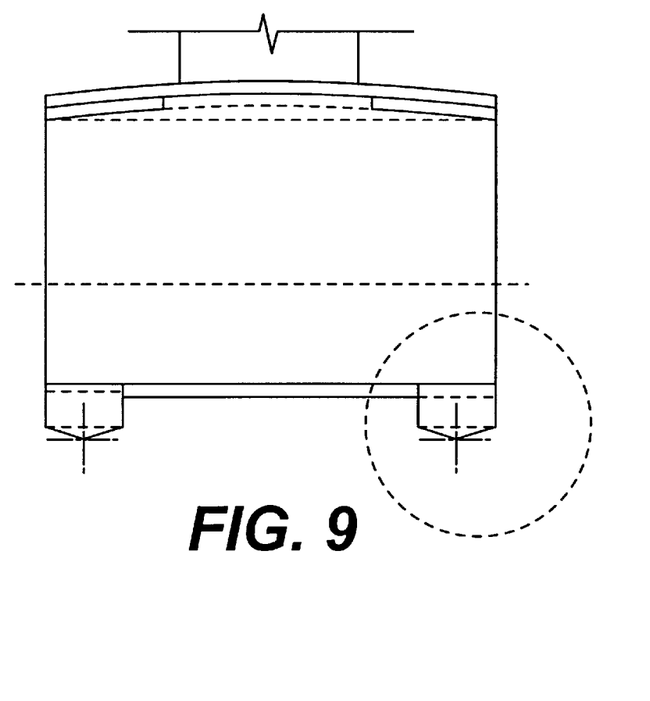
FIG. 9 is a section view showing the cut A—A with a detail view of the inferior plate.
Figure 10:
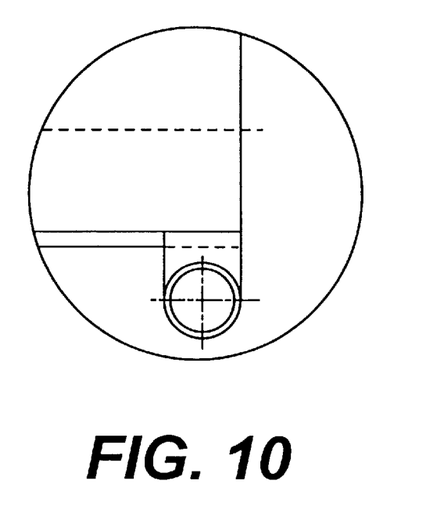
FIG. 10 is a detail view of another form of the inferior plate.
Figure 11:
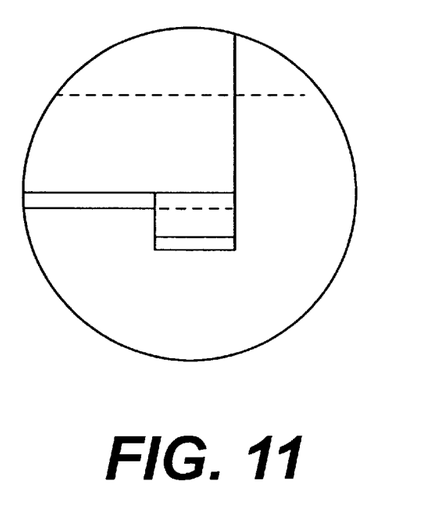
FIG. 11 is a detail view of a third form to the inferior plate.
Figure 12:
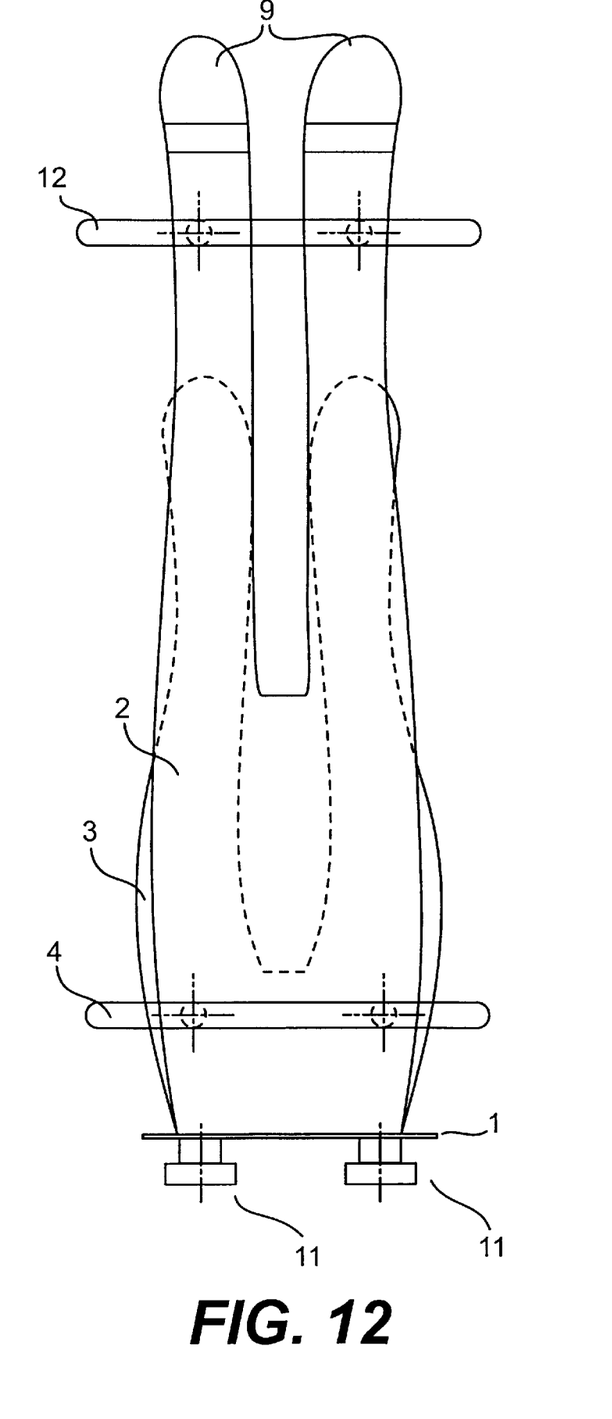
FIG. 12 is a superior view of another modified form of the retractor of the present invention.
Figure 13:
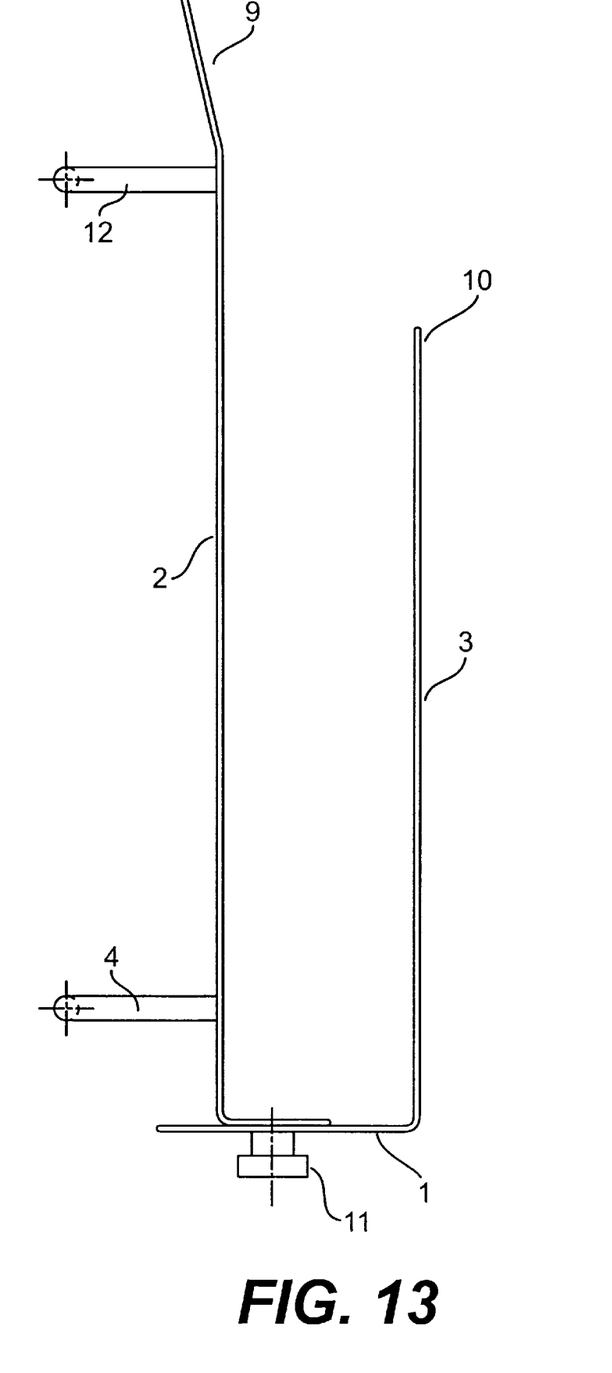
FIG. 13 is a side view of this modification.
Figure 14:
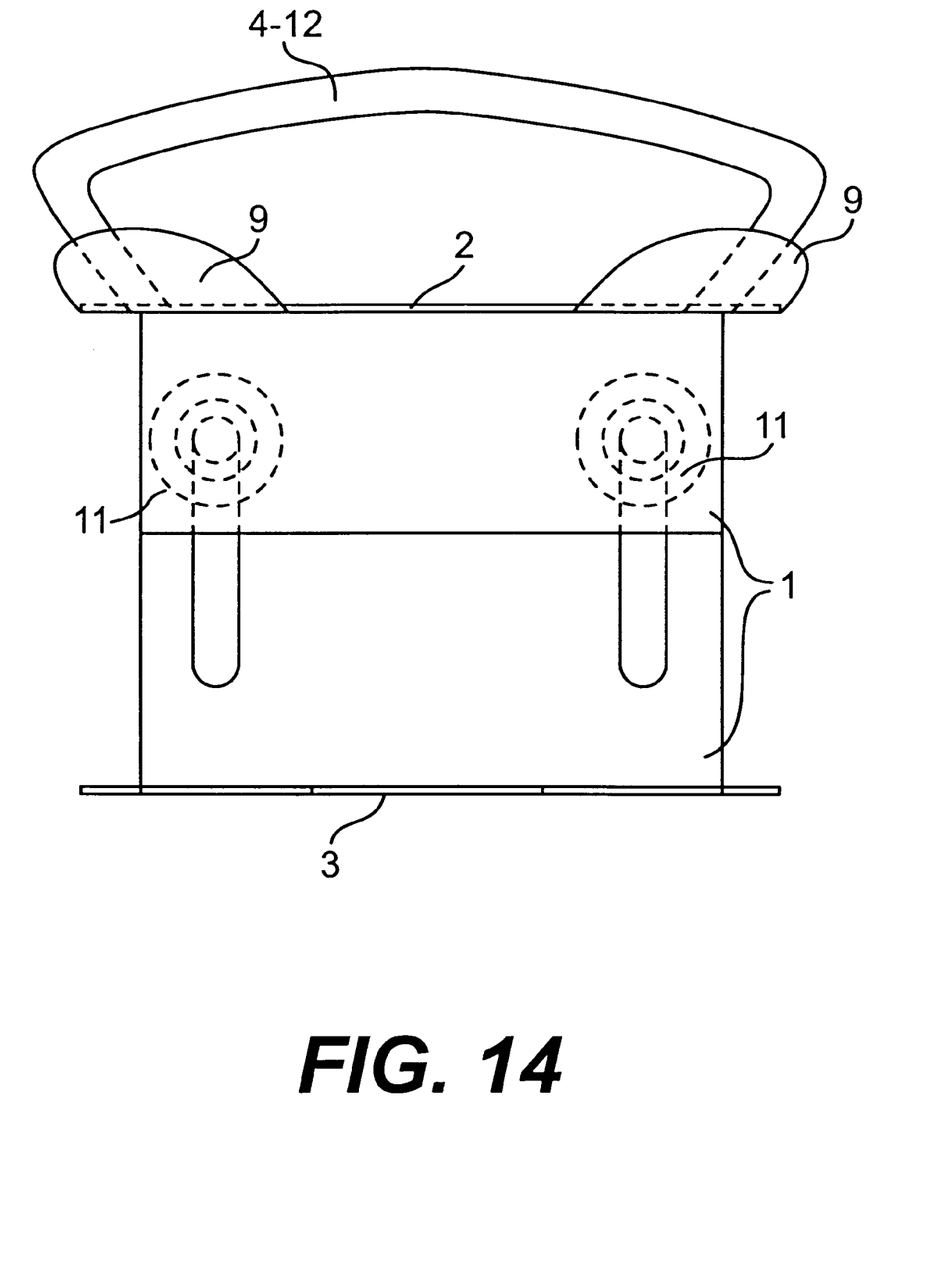
FIG. 14 is a rear view of this modification.

Two modified forms have been developed: A smaller one for general use and for narrow cavities (FIG. 6, FIG. 7, and FIG. 8) with two teeth in each plate and variable forms for the inferior plate indentations as demonstrated in FIG. 9 (beveled), FIG. 10 (cylindrical), and FIG. 11 (flattened); and a bigger one for abdominal wall surgery (FIG. 12, FIG. 13 and FIG. 14) with two indentations in each plate . A has a device 11 is provided to adapt the aperture of the retractor with the thickness of the abdominal wall. An auxiliary handle 12 is used to lift the depth of the flap enough for surgeon maneuvering when reinforcing the abdominal wall musculature with sutures.

While there has been shown and described a preferred embodiment of the hold lever retractor of this invention, it is understood that changes in structure, materials, sizes, and shapes can be made by those skilled in the art without departing from the invention. The invention is definde in the following claims.

What is claimed is:

1. A surgical device used for separating tissue to expose a surgical area which comprises
a plate member which is folded on itself to form a superior plate portion, an inferior plate portion and a folded portion disposed therebetween, said superior plate portion being spaced apart from the inferior plate portion for defining respective proximal and distal ends thereof and for accommodating a layer of tissue therebetween, said superior plate portion being larger than said inferior plate portion and each of said plate portions being divided into a plurality of fingers.

2. The surgical device of claim 1, wherein the fingers of the inferior plate portions extend from the folded portion to the distal ends thereof.

3. The surgical device of claim 2, wherein the fingers of the superior plate portion extend a substantial distance from their distal ends.

4. The surgical device of claim 3, wherein both the superior plate portion and the inferior plate portion have two fingers and the distal ends of the fingers of the superior plate portion are angulated in the upward direction and the distal ends of the fingers of the inferior plate portion are angulated in the downward direction.

5. The surgical device of claim 1, wherein superior plate portions have central fingers and peripheral fingers, said central fingers being more elevated than the peripheral fingers.

6. The surgical device of claim 5, where the difference in elevation becomes more pronounced as the fingers extend toward the distal end.

7. The surgical device of claim 6, wherein the distal ends of the fingers are angulated in the upward direction.

8. The surgical device of claim 1, wherein the inferior plate portion has central fingers and peripheral fingers, said peripheral finger being more elevated than said central fingers.

9. The surgical device of claim 8, wherein the distal ends of the fingers are angulated in the downward direction.

10. The surgical device of claim 1 wherein both the superior plate portion and inferior plate portion have four fingers.

11. The surgical device of claim 1, wherein a handle extends from the superior plate portion near the proximal end thereof.

12. The surgical device of claim 11, wherein an auxiliary handle extends from the superior plate portion near the distal end thereof.

13. The surgical device of claim 1, wherein means are provided for varying the distance at which the superior plate portion is spaced apart from the inferior plate portion.

* * * * *